United States Patent [19]

Cox

[11] Patent Number: 5,272,444
[45] Date of Patent: Dec. 21, 1993

[54] DIELECTRIC CROSS-PLOT WATER CUT MONITORING APPARATUS AND METHOD

[75] Inventor: Percy T. Cox, Houston, Tex.

[73] Assignee: Texaco Inc., White Plains, N.Y.

[21] Appl. No.: 762,188

[22] Filed: Sep. 19, 1991

[51] Int. Cl.$^5$ .................... G01R 27/02; G01R 27/22; G01N 27/06; G01N 27/02

[52] U.S. Cl. ..................... 324/698; 324/664; 324/683; 324/694; 324/704; 324/707; 73/61.44

[58] Field of Search ............... 324/629, 634, 640, 649, 324/664, 689, 691, 694, 696, 698, 704, 705, 713, 709, 721, 722, 438; 73/61.43, 61.44; 364/502

[56] References Cited

U.S. PATENT DOCUMENTS

| 5,014,010 | 5/1991 | Helms et al. ........................ 324/640 |
| 5,070,725 | 12/1991 | Cox et al. ........................... 73/61.1 R |

Primary Examiner—Gerard R. Strecker
Assistant Examiner—Diep Do
Attorney, Agent, or Firm—James J. O'Loughlin; Ronald G. Gillespie

[57] ABSTRACT

The present invention includes a dielectric sensor which provides at least two signals corresponding to the sensed dielectric of a petroleum stream. A temperature sensor also senses the temperature of the petroleum stream and provides a corresponding temperature signal. Cross-plot data arrange the two parameters associated with the petroleum stream dielectric is stored in a memory. The memory is accessed using signals from the dielectric sensor and the temperature sensor to select data from the memory. An output circuit provides a water cut signal in accordance with the selected data.

22 Claims, 3 Drawing Sheets

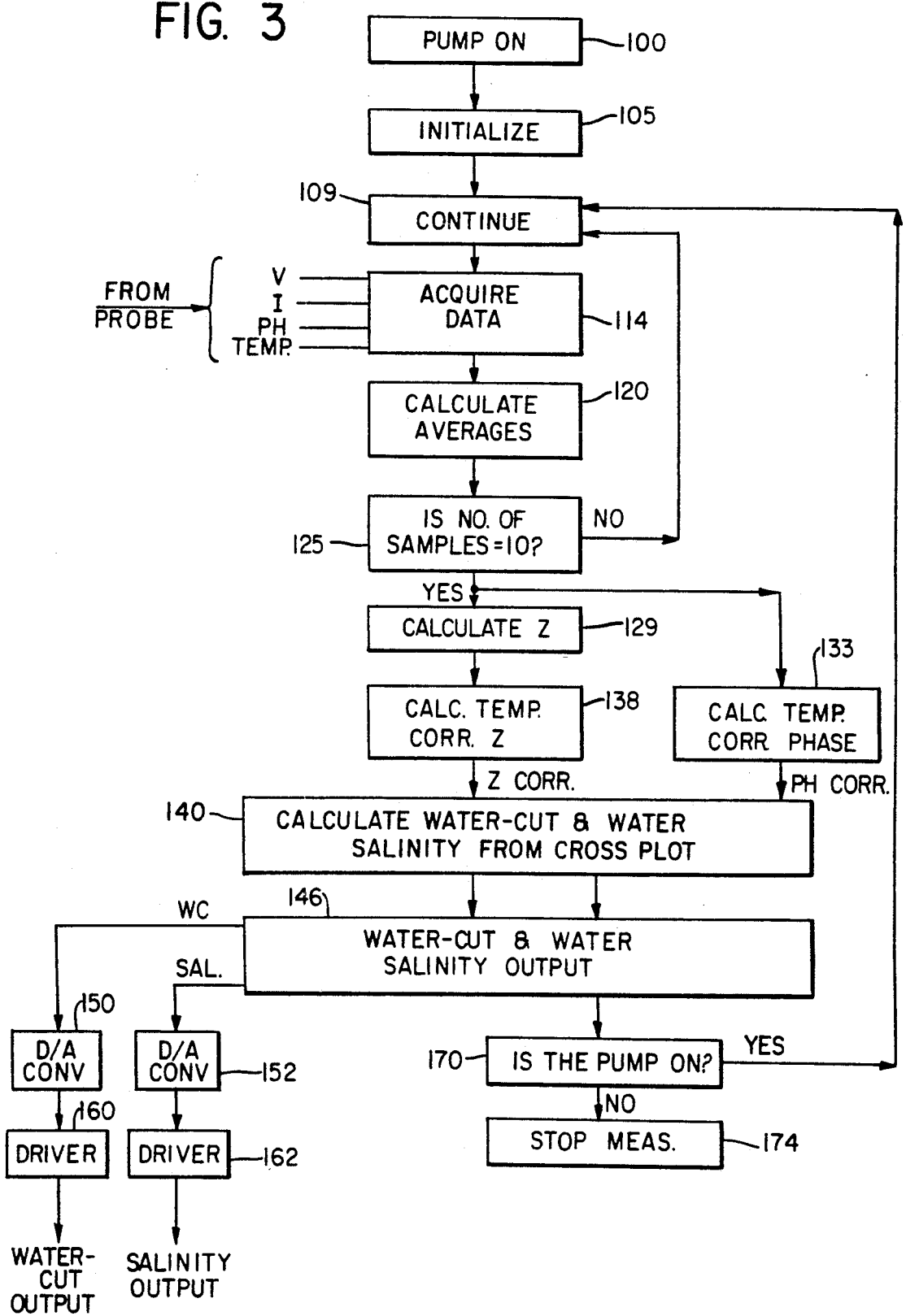

DIELECTRIC CROSS-PLOT WATER CUT MONITORING APPARATUS AND METHOD

BACKGROUND OF THE INVENTION

Field of the Invention

The present invention relates to water cut cross-plot monitoring means and methods and, more particularly, to dielectric water cut monitoring means and methods.

SUMMARY OF THE INVENTION

A water cut monitor includes sensing apparatus which senses at least two parameters of a petroleum stream and provides corresponding sensed parameter signals. Relationships between the two sensed parameters signals and water cuts of fluids having oil and water, for different combinations of the sensed parameter signals, are established. An output network provides an output corresponding to the water cut of the petroleum stream in accordance with the sensed parameter signals and an established relationship.

The objects and advantages of the invention will appear more fully hereinafter from a consideration of the detailed description which follows, taken together with the accompanying drawings where in several embodiments the invention are illustrated by way of example. It is to be expressly understood, however, that the drawings are for illustration purposes only and are not to be construed as defining the limits of the invention.

DESCRIPTION OF THE DRAWINGS

FIG. 3 is a flow diagram of the steps involved in practicing the embodiment with the monitor shown in FIG. 1.

DESCRIPTION OF THE INVENTION

Figure 1:
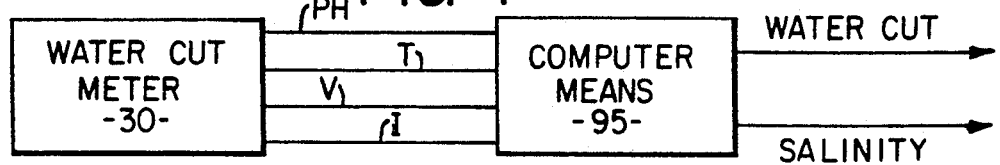
FIG. 1 is a simplified block diagram of a water cut monitor for practicing one embodiment of the invention.
Figure 2:
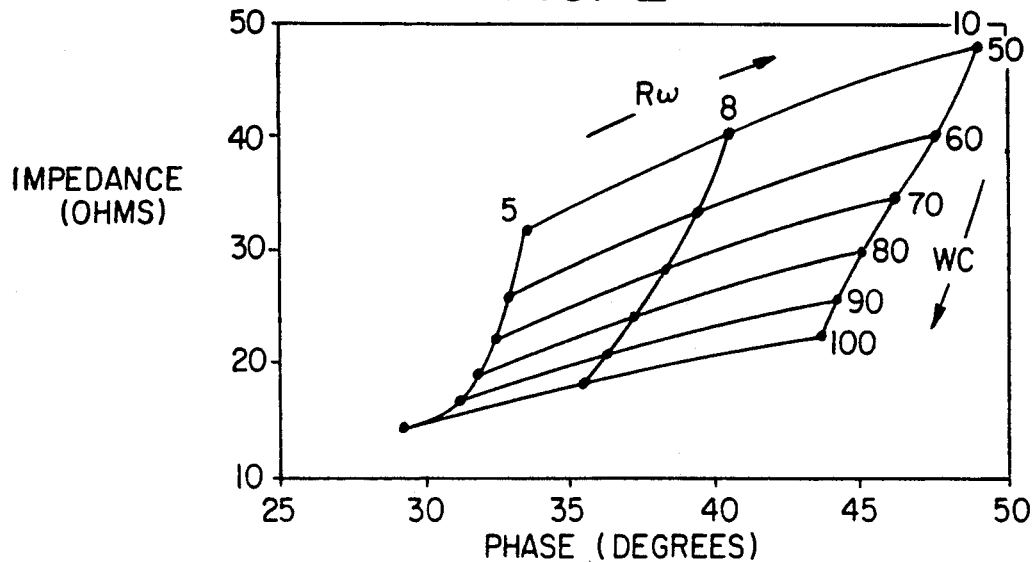
FIG. 2 is a crossplot of the type that is utilized by the monitor shown in FIG. 1.

Referring to FIG. 1, there is shown a system for determining the water cut of a petroleum stream utilizing a Crossplot of Impedance versus Phase. FIG. 2 illustrates the Impedance versus Phase Crossplot method, practiced with the FIG. 1 arrangement, for a range of water-cut from 50% to 100% and for a water resistivity range of 5 ohm-meters to 10 ohm-meters. As seen, each value of water-cut and water resistivity is represented by a unique simultaneous measurement of impedance and phase. Using this method, no water impedance value is required as a reference. The curves of FIG. 2 are for use in a water-continuous emulsion. When the fluid switches to an oil-continuous emulsion, the same two simultaneous measurements are made, with the phase approaching 90 degrees and the impedance quite a bit higher. No additional measurement is required to denote fluid phase change because a unique plot of impedance and phase exists for both water-continuous and oil-continuous emulsions.

In FIG. 1, water cut meter 30, in cooperation with other elements, have been described and disclosed in U.S. patent application 07/405,996 filed Sep. 12, 1989, now U.S. Pat. No. 5,070,725 which is hereby incorporated into the present disclosure. Computer means 95 may be a computer with plotting apparatus. It also may be the computer by itself in which it internally develops a plot and provides it on a screen. But, in any case a plot is developed, as shown in FIG. 2, in which impedance is one axis (Ordinate) and phase is another axis (abscissa). Shown, thereon, is the plot where in one direction the resistance of the water $R_W$ can be determined, or another direction the water cut may be determined. From this plot, which is developed during calibration from empirical data, the computer means 95 determines the resistance of the water $R_W$ and the water cut WC of the petroleum stream.

FIG. 3 shows a software flow diagram for accomplishing the Impedance versus Phase Crossplot Method as shown in FIG. 2. Simply put, the measurement cycle begins with a "pump on" signal which initializes all parameters. Data from the water-cut probe are then acquired and averaged over 10 samples. These data include probe voltage, probe current, the electrical phase angle between probe voltage and probe current, and the probe temperature. The probe impedance and temperature corrected probe impedance are then calculated. The measured electrical phase angle is also temperature corrected. The corrected values of impedance and phase are then used to calculate water-cut and water resistivity (water salinity) using either a look-up table method or curve interpolation software. Water-cut and salinity data are then converted to analog form and then converted to output signals. If the pump is still on, the measurement cycle then repeats. If the pump is no longer on, the measurement cycle ends.

In more detail, FIG. 3 includes a block 100 which indicates that when computer means 95 is prompted, it is programmed to initialize the testing itself as indicated by block 105. We then proceed to "continue" as provided by block 109. The next block 114, "acquire data" causes signals V, I, PH and Temp to be entered into computer means 95. This is done on a sampling basis, as will be explained hereinafter. Block 120 calculates the averages of the acquired data. Block 125 provides for the sampling when it asks the question, "is number of samples equal to 10". If the number of samples is less than 10, the answer is No, and we proceed back to block 109 which is noted before as "continue". Thus the system will keep recycling at least 10 samples are provided, at which time block 125 provides a Yes signal to another block 129, entitled "calculate Z" and to a block 133 entitled "calc temp corr. phase". The output from calculate Z is provided to calculate temp corr Z by a block 138. Blocks 133 and 138 provide signals $ph_{corr}$ and $WC_{corr}$ respectively to a block 140 entitled "calculate water cut and water salinity from cross plot". Signals from block 140 provides a block 146 entitled "water cut and water salinity output". This block 146 provides two output signals, WC and SAL. Signal WC corresponds to the water cut of the fluid stream, while signal SAL to salinity of the water. The two output signals are provided to digital to analog convertors 150, 152 which in turn converts them to analog signals and provides them to drivers 160 and 162 respectively. Drivers 160 and 162 provide output signals corresponding to the water cut output and to the salinity output respectively.

Water cut and water salinity output block 146 also provides a signal to another block 170 which asks the question "is the pump on". If the answer is Yes, a signal if fed back to block 109 to continue the process. When the pump goes off, block 170 provides a signal No, which then provides a signal to block 174 entitled "stop measurement" and the measurement is stopped.

Figure 4:
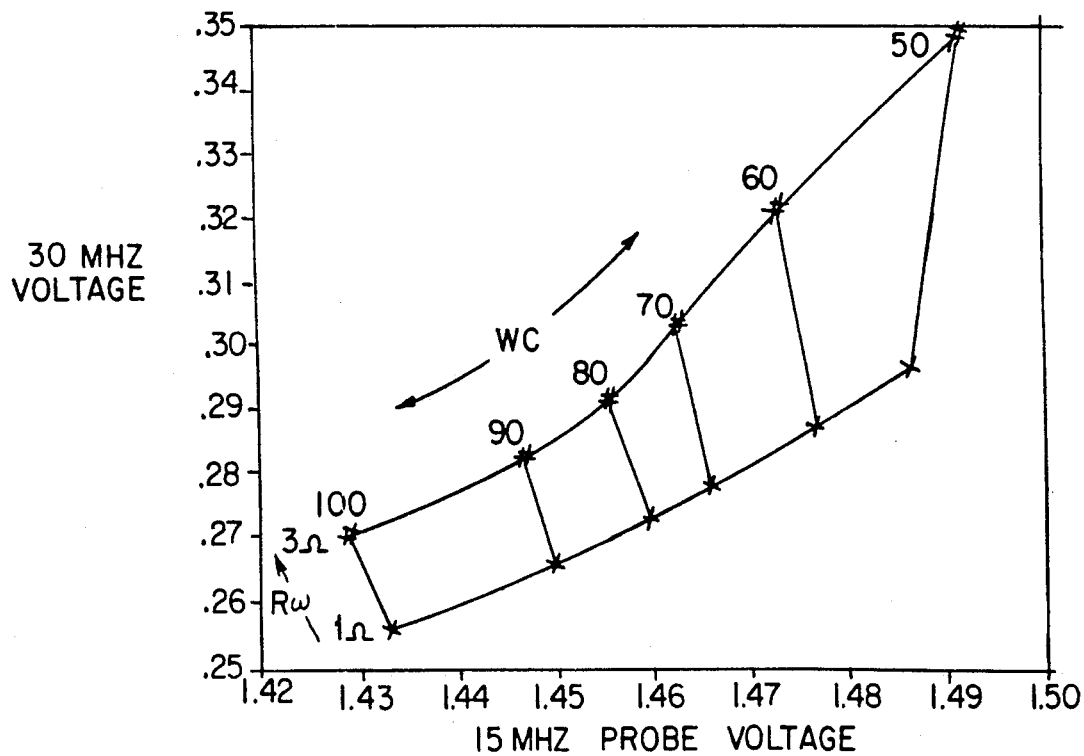
FIG. 4 is a crossplot which represents another embodiment of the present invention, but with the same monitor as shown in FIG. 1 operating at two frequencies.

Another embodiment is shown in FIG. 4, which is a Crossplot utilizing a 30 megahertz voltage and a 15 megahertz voltage. The voltages are obtained by alternating driving the probe in water cut meter 30 with 30 megahertz and 15 megahertz signals from constant current sources and measuring the resulting voltages across the probe. As seen in FIG. 4, both measured voltages are affected by water cut and by water resistivity. The simultaneous measurements again uniquely define values of water cut and water resistivity. The plot shown in FIG. 4 has a 3 ohm line and a 1 ohm line with connecting lines for 100% water cut, 90% water cut, 80% water cut, 70% water cut, 60% water cut and 50% water cut.

Figure 5:
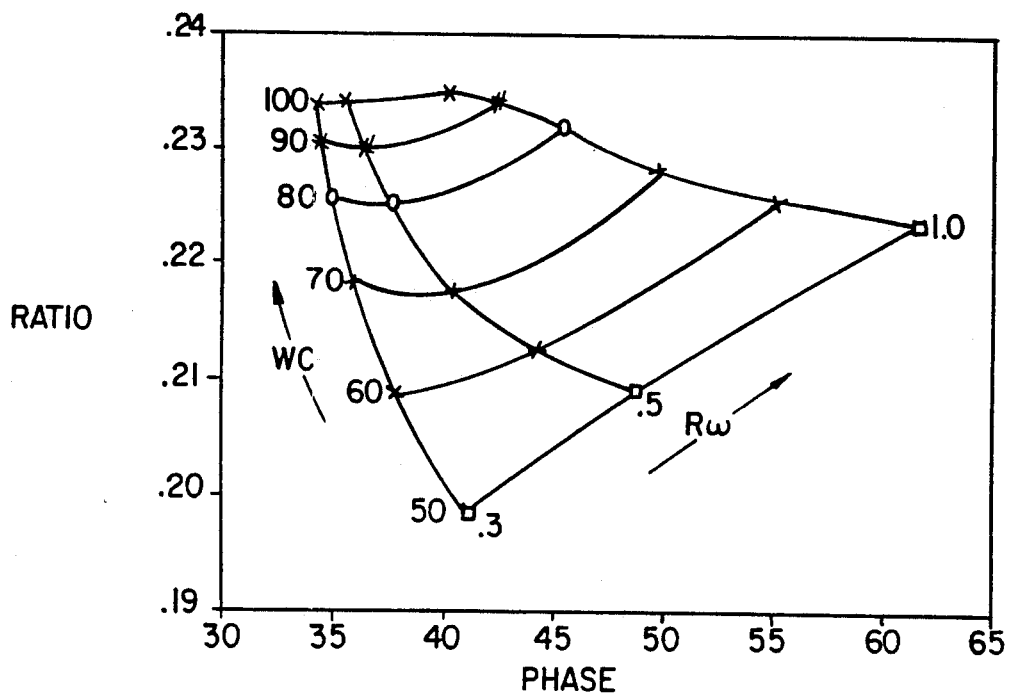
FIG. 5 is a crossplot representative of yet another embodiment of the present invention.

A third crossplot technique, shown in FIG. 5, incorporates amplitude ratio and phase angle. The apparatus utilizing this crossplot technique is shown in FIG. 6.

Figure 6:
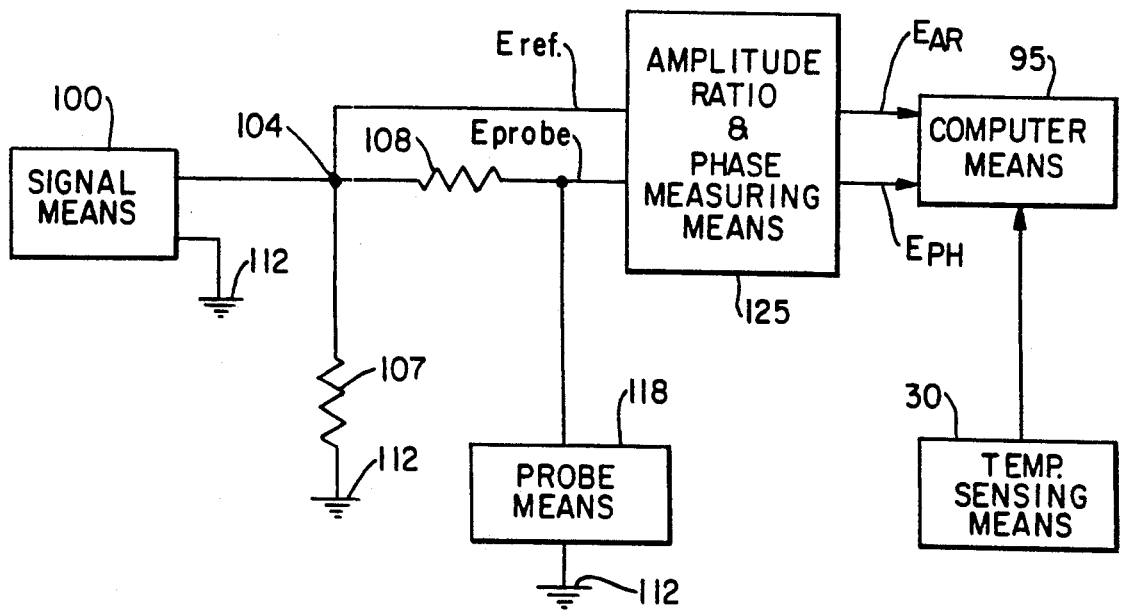
FIG. 6 is simplified block diagram for practicing the embodiment of the present invention represented by FIG. 5.

In FIG. 6, signal means 100 provides a signal to a common connection 104 of a pair of resistors 107, 108. Resistor 107 is also connected to a ground 112 as is signal means 100. Resistor 108 is also connected to probe means 118 and to amplitude ratio and phase measuring means 125 via a common connection 130. A reference signal $E_{ref}$ is developed at connection 104 and is provided to amplitude ratio and phase measuring means 125. Means 125 utilizes signals $E_{ref}$, $E_{probe}$ to provide signals $E_{AR}$, $E_{PH}$ corresponding to the amplitude ratio $E_{probe}/E_{ref}$ of signals $E_{ref}$ and $E_{probe}$ and to the phase difference between signals $E_{ref}$ and $E_{probe}$, respectively. Thus signal $E_{AR}$ provides information related to the ordinate of FIG. 5 while signal $E_{PH}$ provides information related to the abscissa of FIG. 5.

Signal $E_{AR}$, $E_{PH}$ are provided to computer means 95 which also receives a signal from a temperature sensing means corresponding to the sensed temperature of the petroleum stream.

The important advantage of using these crossplot methods is that no additional measurement is required to determine fluid phase, and no reference such as measuring the 100 percent water impedance is required. In order for the method to be accurate, fluid temperature must be carefully monitored and used to correct all measurements to a single temperature.

Calibration curves would be required over the water resistivity range expected and should be made using crude oil from the wells to be monitored. This calibration may be made under controlled conditions in a laboratory flow loop.

What is claimed:

1. A water cut monitor comprising:
   sensing means for sensing at least two parameters of a petroleum stream and providing sensed parameter signals corresponding thereto,
   cross-plot means for establishing a cross-plot between the two sensed parameter signals and water cuts of fluids having oil and water for different combinations of the sensed parameter signals, and
   output means connected to the sensing means and to the cross-plot means for providing an output corresponding to the water cut of the petroleum stream in accordance with the sensed parameter signals and the cross-plot.

2. A monitor as described in claim 1 in which the sensed electrical parameters are the dielectric constant and resistivity of the petroleum stream and the sensed parameter signals are representative of the impedance of the petroleum stream and the impedance phase angle.

3. A monitor as described in claim 2 in which the sensing means further comprises means for sensing the temperature of the petroleum stream and providing a temperature signal representative thereof, and
   the cross-plot means establishes the crossplots as between the temperature, the two sensed parameter signals and the water cuts for different combination of temperature and the two sensed parameter signals.

4. A monitor as described in claim 3 in which the cross-plot means includes:
   memory means for storing water cut data for different combinations of temperatures, impedances and phase angles,
   means for deriving a cross-plot from the stored data, and
   the output means includes determining means connected to the sensing means and to the memory means for determining a water cut in accordance with the derived cross-plot, and
   means for providing the water cut output in accordance with the determined water cut.

5. A monitor as described in claim 4 in which the memory means has stored water salinity data for different combinations of temperatures, impedance and phase angle;
   the determining means determines a water salinity in accordance with the derived crossplot; and
   the output means provides an output corresponding to the salinity of the water in accordance with the determined water salinity.

6. A monitor as described in claim 4 in which the memory means has stored water resistivity data for different combinations of temperatures, impedances and phase angles;
   the determining means determines a water resistivity in accordance with the derived cross-plot; and
   the output means provides an output corresponding to the resistivity of the water in accordance with the determined water resistivity.

7. A water cut monitor comprising:
   sensing means for sensing a parameter of a petroleum stream when operated at two different frequencies and providing sensed voltages corresponding thereto,
   cross-plot means for establishing a crossplot of water cuts for different combinations of sensed voltages, and
   means for providing an output corresponding to the water cut of the petroleum stream in accordance with the crossplot derived in accordance with the sensed voltages from the sensing means.

8. A monitor as described in claim 7 in which the sensing means further comprises means for sensing the temperature of the petroleum stream and providing a temperature signal representative thereof, and
   the cross-plot means establishes a crossplot of water cuts for different combination of temperature signals and the two sensed voltages.

9. A monitor as described in claim 8 in which the cross-plot means includes:
   memory means for storing water cut data for different combinations of the temperature signal and the two sensed voltages,
   deriving means for deriving a cross-plot from the stored data, and
   the output means includes determining means connected to the sensing means and to the deriving means for determining a water cut in accordance with the derived cross-plot, and
   means for providing the water cut output in accordance with the determined water cut.

10. A water cut monitor comprising:
   reference means for providing a reference signal,
   probe means located in a petroleum stream and connected to the reference means for affecting the reference signal as a function of the dielectric constant of the petroleum stream to provide a sensed signal,
   signal means connected to the reference means and to the probe means for providing a ratio signal corresponding to the ratio of the sensed signal to the reference signal, and a phase signal corresponding to the phase difference between the sensed signal and the reference signal,
   cross-plot means for establishing a cross-plot of water cuts of fluids having oil and water for different combinations of ratio signals and phase signals, and
   output means connected to the establishing means and to the signal means for providing an output corresponding to the water cut of the petroleum stream in accordance with the established cross-plot using the ratio signal and phase signal from the signal means.

11. A monitor as described in claim 10 further comprising means for sensing the temperature of the petroleum stream and providing a temperature signal representative thereof, and
   the cross-plot means establishes the cross-plot as between the temperature, the ratio signal, the phase signal and the water cuts for different combination of temperatures, ratio signals and phase signals.

12. A monitor as described in claim 11 in which the water cut means includes:
   memory means for storing water cut data for different combinations of temperatures, ratio signals and phase signals,
   deriving means for deriving a cross-plot from the stored data
   the output means includes determining means connected to the sensing means and to the deriving means for determining a crossplot water cut in accordance with the cross-plot, the ratio signal, the phase signal and the temperature signal, and
   means for providing the water cut output in accordance with the determined water cut.

13. A monitor as described in claim 12 in which the memory means has stored water salinity data for different combinations of temperatures, ratio signal and phase signals;
   the determining means a water salinity in accordance with the crossplot, ratio signal, the phase signal and the temperature signal; and
   the output means provides an output corresponding to the salinity of the water in accordance with the determined water salinity.

14. A monitor as described in claim 12 in which the memory means has stored water resistivity data for different combinations of temperatures, ratio signals and phase signals;
   the determining means determines a water resistivity in accordance with the cross-plot, the ratio signal, the phase signal and the temperature signal; and
   the output means provides an output corresponding to the resistivity of the water in accordance with the determined water resistivity.

15. A water cut monitoring method comprising the steps of:
   sensing at least two parameters of a petroleum stream with sensing means,
   having the sensing means provide sensed parameter signals corresponding to the sensed parameters,
   establishing a cross-plot in computer means between the two sensed parameter signals and water cuts of fluids having oil and water for different combinations of the sensed parameter signals, and
   having the computer means provide an output corresponding to the water cut of the petroleum stream being monitored in accordance with the sensed parameter signals and an established relationship.

16. A method as described in claim 15 in which the sensed electrical parameters are the dielectric constant and resistivity of the petroleum stream and the sensed parameter signals are representative of the impedance of the petroleum stream and the impedance phase angle.

17. A method as described in claim 16 in which the sensing step further comprises the steps of:
   sensing the temperature of the petroleum stream with temperature sensing means and
   providing a temperature signal representative thereof; and
   the establishing step establishes the cross-plot as between the temperature, the two sensed parameter signals and the water cuts for different combination of temperature and the two sensed parameter signals.

18. A water cut monitoring method comprising the steps of:
   sensing a parameter of a petroleum stream with sensing means operated at two different frequencies at different times,
   providing sensed voltages corresponding sensed parameters,
   establishing a cross-plot in computer means from water cuts for different combinations of sensed voltages, and
   providing an output with the computer means corresponding to the water cut of the petroleum stream in accordance with the cross-plot and the sensed voltages.

19. A method as described in claim 18 in which the sensing step further comprises the step of sensing the temperature of the petroleum stream with temperature sensing means,
   providing a temperature signal representative of the sensed temperature; and
   the establishing step includes establishing the cross-plot as between the temperature signal, the two sensed voltages and the water cuts for different combination of temperature signals and sensed voltages.

20. A method as described in claim 19 in which the establishing step includes:

storing cross-plot data in memory means for different combinations of temperature signals and sensed voltages, the output steps includes determining a water cut in accordance with the sensed parameter signals and the temperature signal, and providing the water cut output in accordance with the selected water cut.

21. A water cut monitoring method comprising the steps:

providing a reference signal from reference means, locating probe means in a petroleum stream, said probe means being connected to the reference means and affecting the reference signal as a function of the dielectric constant of the petroleum stream to provide a sensed signal, providing a ratio signal, using ratio signal means corresponding to the ratio of the sensed signal to the referenced signal, providing a phase signal, using phase signal means, corresponding to the phase difference between the sensed signal and the reference signal, establishing a cross-plot of water cuts of fluids having oil and water with computer means for different combinations of ratio signals and phase signals, and providing an output from the computer means corresponding to the water cut of the petroleum stream in accordance with an established crossplot determined using the ratio signal and phase signal from the signal.

22. A method as described in claim 21 further comprising the steps of:

sensing the temperature of the petroleum stream with temperature sensing means, and providing a temperature signal representing of the sensed temperature; and the establishing step includes establishing the relationships as between the temperature, the ratio signal, the phase signal and the water cuts for different combination of temperatures, ratio signals, and phase signals.

* * * * *